United States Patent [19]
Ito

[11] Patent Number: 5,630,667
[45] Date of Patent: May 20, 1997

[54] MODEL AND METHOD FOR PREDICTING HEAT CRACKING OF HEAT-RESISTANT MEMBERS

[75] Inventor: Kenji Ito, Moka, Japan

[73] Assignee: Hitachi Metals Ltd, Tokyo, Japan

[21] Appl. No.: 413,160

[22] Filed: Mar. 29, 1995

[30] Foreign Application Priority Data

Mar. 30, 1994 [JP] Japan .................................. 6-060806

[51] Int. Cl.⁶ .............................. G01N 3/60; G01N 25/72; G01M 19/00
[52] U.S. Cl. ................................. 374/57; 73/866.4
[58] Field of Search .................. 374/142, 57, 4, 374/5; 73/804, 866.4

[56] References Cited

U.S. PATENT DOCUMENTS

| | | | |
|---|---|---|---|
| 3,964,313 | 6/1976 | Connick | 374/134 |
| 4,711,131 | 12/1987 | Hopkins | 73/866.4 |
| 5,048,346 | 9/1991 | Yano et al. | 73/804 |

FOREIGN PATENT DOCUMENTS 3-28731  2/1991  Japan .

OTHER PUBLICATIONS

D MEC Modeling, D MEC Ltd, p. 3, Figs. 1–6, w/translation (Aug. 1993).

Nikkan Kogyo Shinbun Mar. 11, 1994 w/translation.

Optimization of Casting Design, 60th World Foundry Congress, The Hague/Netherlands 1993.

*Primary Examiner*—Diego F. F. Gutierrez
*Attorney, Agent, or Firm*—Finnegan, Henderson, Farabow, Garrett & Dunner

[57] ABSTRACT

The heat cracking of a heat-resistant member is predicted by (a) producing a model having a similar shape to that of the heat-resistant member from a photo-set resin having a thermal conductivity of 0.1–0.2 W/m·K, (b) introducing a hot air at a temperature of 50° C. or higher and lower than a softening point of the photo-set resin into the model, (c) measuring a temperature in each portion of the model by a thermal image analyzer, (d) measuring the changes of temperature distribution in the model with time to find whether or not there are overheated portions in the model, and (e) determining the overheated portions as portions in which heat cracking may take place.

3 Claims, 6 Drawing Sheets

MODEL AND METHOD FOR PREDICTING HEAT CRACKING OF HEAT-RESISTANT MEMBERS

FIELD OF THE INVENTION

The present invention relates to a model and a method for predicting the heat cracking of a heat-resistant member adapted to be partially or totally heated to as high a temperature as 500° C. or higher, particularly a method of blowing a hot air into a resin model having a completely similar shape to that of the heat-resistant member to measure the temperature distribution and thermal strain distribution of the resin model thereby predicting the heat cracking of the heat-resistant member.

BACKGROUND OF THE INVENTION

Heat-resistant members subjected to repeated heating and cooling include for instance exhaust equipment such as exhaust manifolds, etc. for use in internal engines of automobiles. Exhaust equipment thermally expands by exposure to a high temperature during engine operation and thermally shrinks by cooling by the air when the engine is stopped. This repeated heating and cooling exerts a large thermal load to the exhaust equipment. When the thermal load becomes excessive, the heat-resistant member is subjected to heat deformation and/or heat cracking, causing problems such as gas leaks, etc.

However, since there are many heat-resistant members having extremely complicated shapes, it is generally difficult to predict the generation of heat cracks. Accordingly, test models of heat-resistant members have conventionally been produced from cast iron or cast steel and tested under practical heating conditions, suffering from the problems of extremely long test time and labor.

A main cause of cracks generated in the exhaust equipment repeatedly subjected to high-temperature heating and cooling is that local overheat or heat accumulation (hereinafter referred to as "hot spot") takes place in the exhaust equipment during temperature elevation. Thus, if the positions of the hot spots can be located accurately, it would be possible to predict where cracking may take place. Positions at which large thermal strain is concentrated during temperature elevation correspond to portions in which there is a large plastic compression deformation affecting thermal deformation and heat cracking. Thus, if positions at which thermal strain is concentrated can be located accurately, it would be possible to predict the thermal deformation and heat cracking of the heat-resistant members.

Under such circumstances, the applicant previously proposed a model made of a polyurethane foam similar to a heat-resistant member (Japanese Patent Laid-Open No. 3-28731). In Japanese Patent Laid-Open No. 3-28731, a hot air is introduced into a polyurethane foam model with its inlets and outlets restrained to measure a temperature distribution on a model surface by a thermal image analyzer and also to measure a thermal strain distribution by strain gauges attached to the model surface, thereby predicting portions in which heat cracking may take place.

However, the polyurethane foam model has as small a thermal conductivity as about $1/2500$ of those of heat-resistant cast steel or heat-resistant cast iron. Accordingly, when a polyurethane foam is used for a thermal analysis model, it can achieve only an extremely small thermal conductivity. Thus, comparing with the measurement results of temperature distribution of a practical heat-resistant member, accuracy should be improved in the measurement of transitional temperature changes occurring in a short period of time, though the polyurethane foam model may be effectively used in a stationary measurement. Also, since the heat resistance of the polyurethane foam is practically 50° C. or lower, the temperature distribution and strain level on a thermal analysis model surface are easily affected by a temperature variation in a measurement chamber.

Further, to produce a thermal analysis model from a polyurethane foam, it is necessary to read complicated drawings of a heat-resistant member to cut a polyurethane foam block into a three-dimensional model. However, this requires an extremely high skill and a long time which is usually about two or three weeks.

Accordingly, an object of the present invention is to provide a thermal analysis model with which the positions of local hot spots and thermal strain affecting the durability of a heat-resistant member subjected to heating and cooling can be highly accurately located, thereby being capable of predicting the heat cracking of the heat-resistant member.

Another object of the present invention is to provide a method for predicting portions of a heat-resistant member in which heat cracking may take place by means of a three-dimensional thermal analysis model, thereby determining a structure of the heat-resistant member free from heat cracking.

SUMMARY OF THE INVENTION

As a result of the intense research in view of the above objects, the inventor has found that a three-dimensional model for thermal analysis can easily be formed by irradiating laser beams to a liquid photo-setting resin according to CAD data, and that since the resultant photo-set resin model has a larger thermal conductivity than that of a polyurethane foam model and an appropriate heat resistance, it can be used for an accurate thermal analysis. The present invention has been accomplished based on this finding.

Thus, the model for predicting the heat cracking of a heat-resistant member according to the present invention has a similar shape to that of the heat-resistant member and is made of a photo-set resin having a thermal conductivity of 0.1–0.2 W/m·K.

The first method for predicting the heat cracking of a heat-resistant member according to the present invention comprises the steps of (a) producing a model having a similar shape to that of the heat-resistant member from a photo-set resin having a thermal conductivity of 0.1–0.2 W/m·K, (b) introducing a hot air at a temperature of 50° C. or higher and lower than a softening point of a photo-set resin into the model, (c) measuring a temperature in each portion of the model by a thermal image analyzer, (d) measuring the changes of temperature distribution in the model with time to find whether or not there are overheated portions in the model, and (e) determining the overheated portions as portions in which heat cracking may take place.

The second method for predicting the heat cracking of a heat-resistant member according to the present invention comprises the steps of (a) producing a model having a similar shape to that of the heat-resistant member from a photo-set resin having a thermal conductivity of 0.1–0.2 W/m·K, (b) attaching a strain gauge to each portion of the model, (c) introducing a hot air at a temperature of 50° C. or higher and lower than a softening point of the photo-set resin into the model with inlet and outlet openings thereof restrained, (d) measuring a thermal strain distribution in the model from the output of the strain gauges, and (e) determining portions in which the thermal strain exceeds a predetermined level as portions in which heat cracking may take place.

Since the photo-set resin model has a higher heat resistance than the polyurethane foam, a hot air at a temperature of 50° C. or higher and lower than a softening point of a photo-set resin can be introduced into the model continuously or intermittently. Also, since the photo-set resin model has a larger thermal conductivity than a polyurethane foam model, the photo-set resin model shows a larger temperature elevation speed, making it possible to clearly observe hot spots occurring during the temperature elevation.

The photo-set resin model is formed in a three-dimensional shape by irradiating laser beams to a surface of a liquid photo-setting resin according to contour data produced from a three-dimensional shape similar to the heat-resistant member by a computer. Thus, the photo-set resin model has an extremely accurate three-dimensional shape and can be produced in a short period of time without a skilled laborer cutting a model block referring to a two-dimensional drawing.

When this photo-set resin model is used for the prediction of the heat cracking of a heat-resistant member, the variation of the temperature distribution with time transitionally occurring in the photo-set resin model is analyzed by an infrared thermal image analyzer, etc. to locate the hot spots generated in the heat-resistant member. According to experiments by the inventor, the positions of hot spots in the photo-set resin model extremely well correspond to the positions of heat cracking. Accordingly, by locating the positions of hot spots in the photo-set resin model, it is possible to accurately predict the positions of heat cracking in the heat-resistant member. In addition, by measuring and analyzing the variation of a thermal strain distribution with time occurring in the photo-set resin model by a strain-measuring apparatus such as a static strain-measuring apparatus or strain gauges, the positions of thermal strain concentration in the heat-resistant member can be determined. Examining the analysis results of both hot spots and thermal strain, more accurate prediction of heat cracking positions can be achieved.

DETAILED DESCRIPTION OF THE PREFERRED EMBODIMENTS

Figure 1:
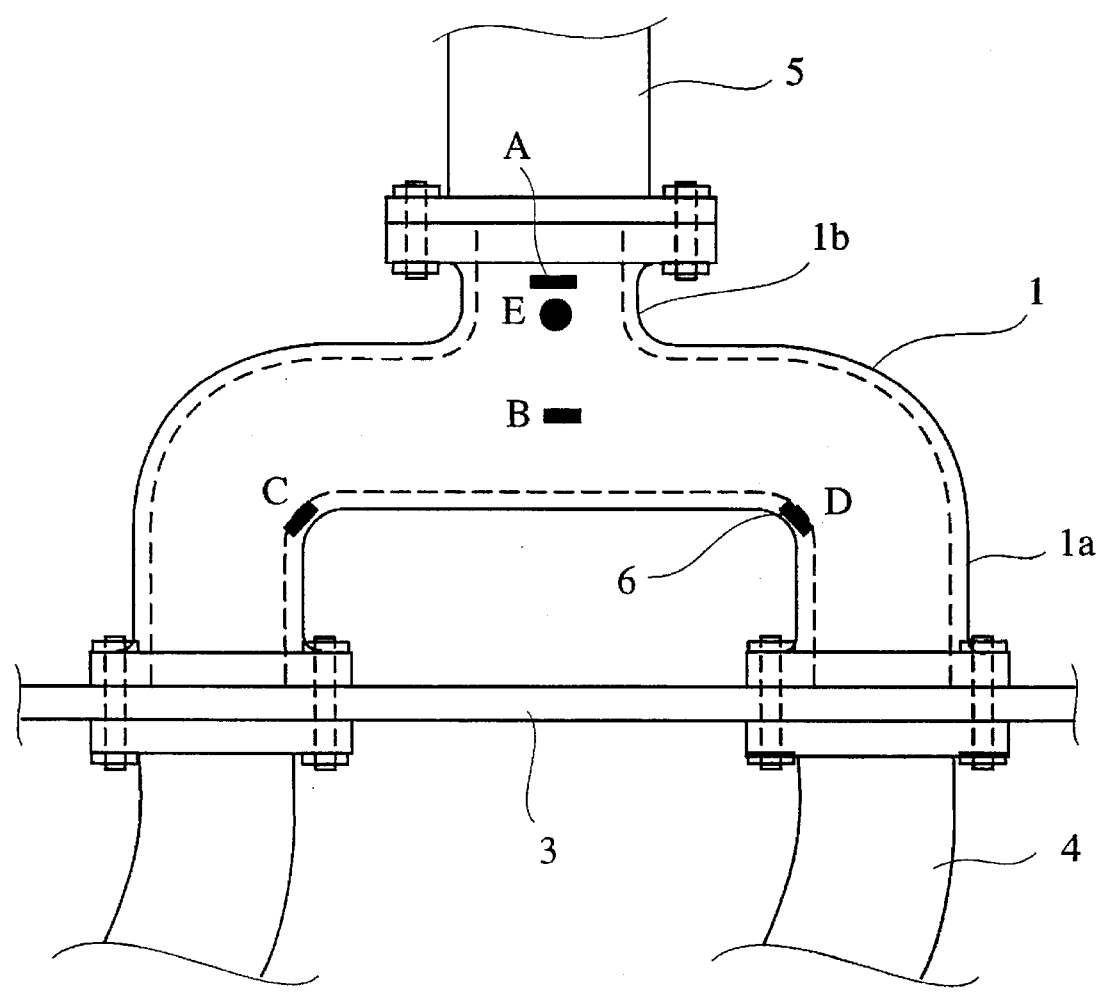
FIG. 1 is a schematic front view showing a thermal analysis using a photo-set resin model according to one embodiment of the present invention.

The present invention will be described in detail referring to the drawings attached hereto.

[1] Photo-Set Resin Model (1) Composition

The thermal analysis model of the present invention is produced from a liquid photo-setting resin which can be rapidly cured by laser beams. The photo-setting resins may be a radical type or a cation type. The radical-type photo-setting resins include urethane acrylate, epoxy acrylate, polyester acrylate, polyether acrylate, etc., and the cation-type photo-setting resins include epoxy resins, vinyl ether resins, etc. Among them, the radical-type photo-setting resins such as urethane acrylate are preferable from the viewpoint of thermal conductivity, strength, heat resistance and handling, etc.

In the case of radical-type photo-setting resins such as urethane acrylate, epoxy acrylate, polyester acrylate, polyether acrylate, the photo-setting resin is in the form of an oligomer containing a reactive diluent, a photo-initiator, etc. Preferably, the photo-setting oligomer is 40–80 weight %, the reactive diluent is 10–50 weight %, and the photo-initiator is 1–10 weight %. The reactive diluent is preferably monofunctional or polyfunctional acrylate, and the photo-initiator may be usual radical initiators.

(1) Properties (a) Thermal Conductivity

The photo-set resin model is integrally constituted by a photo-set resin having a thermal conductivity of 0.1–0.2 W/m·K, preferably 0.13–0.17 W/m·K. On the other hand, the polyurethane foam has a thermal conductivity of about 0.02 W/m·K, and heat-resistant cast steel and high-Si cast iron have a thermal conductivity of 17–26 W/m·K. Thus, the thermal conductivity of the photo-set resin is as small as about 1/100 to 1/200 of that of the heat-resistant iron and as large as about 10 times that of the polyurethane foam. With the thermal conductivity within the above range, there is substantially no diffusion of heat given by the hot air from the inner wall to the outer surface, enabling hot spots to occur accurately on a model surface. If the thermal conductivity of a model is small like a polyurethane foam, a heat diffusion would largely take place during heat conduction, decreasing a temperature gradient on a model surface, which in turn makes it difficult to observe hot spots exactly, if any. On the other hand, if the thermal conductivity of a model is extremely high like heat-resistant cast steel and high-Si cast iron, a transitional temperature gradient on the surface would disappear quickly, making it impossible to observe the transitional temperature distribution.

(b) Heat Resistance

While the polyurethane foam is thermally deformed by a hot air at 50° C. or higher, the photo-set resin is not subjected to a thermal deformation even by a hot air at 50° C. or higher. The upper limit of a hot air temperature is preferably a thermal deformation temperature of the photo-set resin or lower, it may exceed the thermal deformation temperature if the blowing time of the hot air is short, because the photo-set resin having a higher thermal conductivity as compared with the polyurethane foam is warmed quickly, generating hot spots in a short period of time. Specifically, the temperature range of the hot air is preferably 50–200° C.

(3) Production Method

Figure 2:
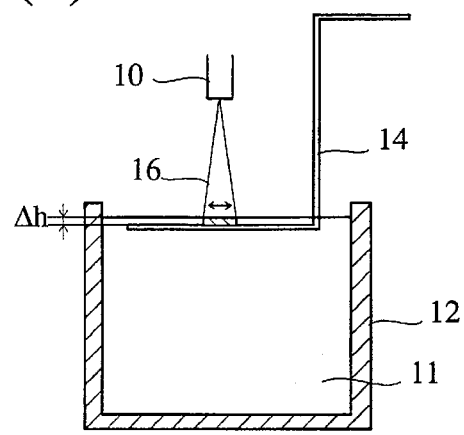
FIGS. 2(a), 2(b), 2(c), and 2(d) are schematic views showing one example of the production of a photo-set resin model.
Figure 2:
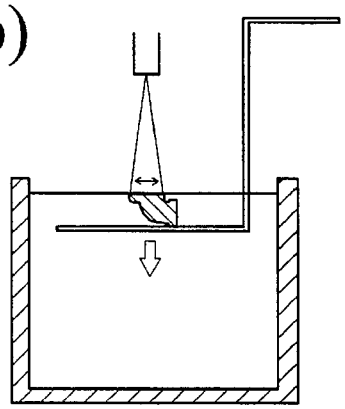
Figure 2:
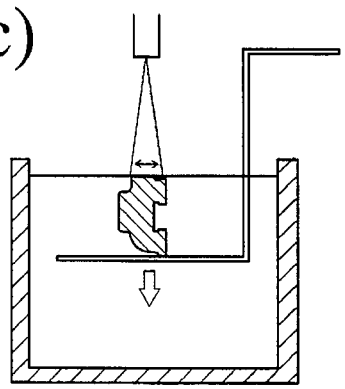
Figure 2:
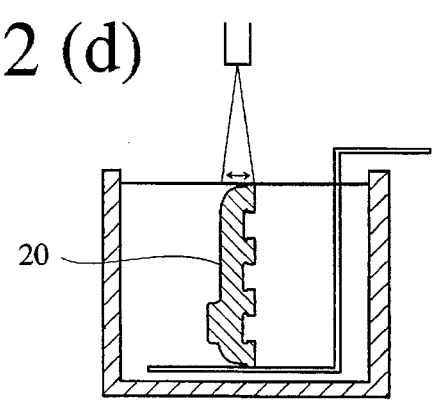

The production of a photo-set resin model is explained with a four-cylindered exhaust manifold in FIG. 2. First, CAD data showing a three-dimensional shape similar to the four-cylindered exhaust manifold are supplied into a computer by which they are sliced to provide contour data each having a thickness ($\Delta h$) of 0.2 mm. The slice thickness ($\Delta h$) may be selected within the range of 0.05–0.5 mm.

An elevator 14 is disposed in a vessel 12 containing a liquid photo-setting resin 11, and a laser (for instance, argon laser) 10 is positioned on a surface of the liquid photo-setting resin 11. The first depth of the elevator 14 corresponds to the slice thickness ($\Delta h$). Under this condition, laser beams 16 are irradiated and scanned on a surface of the liquid photo-setting resin 11 according to the contour data supplied from the computer. Portions of the liquid photo-setting resin 11 irradiated by the laser beams 16 are cured from a liquid to a solid, thereby forming on the elevator 14 a layer of a photo-set resin (thickness: $\Delta h$) having a cross-sectional shape similar to that of the four-cylindered exhaust manifold (step (a)).

Next, the elevator 14 is lowered stepwise by a distance corresponding to the slice thickness ($\Delta h$) to accumulate a solid layer (thickness: $\Delta h$) having a cross-sectional shape corresponding to the contour data one after another (steps (b)–(c)). By repeating these steps, a photo-set resin model 20 having a three-dimensional shape similar to that of the four-cylindered exhaust manifold is formed (step (d)).

The resultant photo-set resin model 20 is subjected to a post-cure treatment, if necessary, for stabilization. Since the model is directly produced from the three-dimensional data of the heat-resistant member, production steps do not require skilled labor, and the resultant model has an extremely accurate shape.

[2] Thermal Analysis Using Photo-Set Resin Model

FIG. 1 is a front view showing the thermal analysis model made of a photo-set resin according to one embodiment of the present invention. The photo-set resin model 1 has branch pipes 1a each having an inlet opening and a stem pipe 1b having an outlet opening. The inlet opening is connected to an adapter pipe 4 via a frame 3 of a hot air-blowing apparatus. The adapter pipe 4 preferably has a substantially similar shape to that of an actual exhaust pipe so that a hot air introduced into the model through the inlet opening is oriented in the same direction as in the actual member. With this structure, hot spots can appear accurately on the photo-set resin model 1. The outlet opening of the model is connected to an exhaust pipe 5. The exhaust pipe 5 also preferably has a substantially similar shape to that of an actual exhaust pipe. By discharging the hot air outside a measurement atmosphere, it is possible to maintain the measurement atmosphere at a constant temperature.

Strain gauges 6 are attached to a surface of the photo-set resin model 1 at predetermined points A, B, C, D, E ... at which thermal strain is likely to occur. In the case of measuring hot spots, no strain gauges 6 are preferably attached from the viewpoint of measurement accuracy, but the strain gauges 6 may be attached to the model from the beginning in the case of simultaneous measurement of hot spots and thermal strain.

Figure 3:
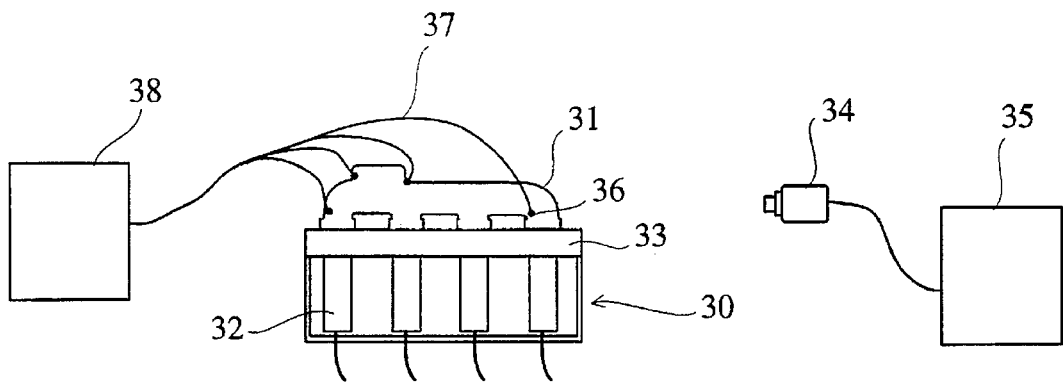
FIG. 3 is a schematic front view showing an apparatus for measuring the temperature distribution and thermal strain distribution of a photo-set resin model.

FIG. 3 shows an apparatus for measuring the temperature distribution and thermal strain distribution of a photo-set resin model for the purpose of heat cracking prediction of a heat-resistant member. A photo-set resin model 31 formed similarly to the heat-resistant member (for instance, four-cylindered exhaust manifold) is fixed to a blower apparatus 30 equipped with a hot air blower (for instance, commercially available dryer) 32 and an adapter 33 having a desired tubular shape. A thermal image camera 34 is connected to a thermal image analyzer 35 equipped with a data recorder and an analyzer. The photo-set resin model 31 is provided with strain gauges 36 at predetermined surface points, from which lead wires 37 are connected to a static strain measuring apparatus 38. The thermal image analyzer 35 and the static strain measuring apparatus 38 are connected to a personal computer (not shown) in which measurement data are analyzed and treated for image display. When the photo-set resin model 1 is heated to a higher temperature, the hot air blower 2 is preferably constituted by a plurality of industrial hot air blowers.

As in the case of the model shown in FIG. 1, a hot air supplied from the hot air blower 32 is introduced into the branch pipes of the photo-set resin model 31 via the adapter 33 having a desired tubular shape, and discharged from a stem pipe of the photo-set resin model 31 to the outside (see FIG. 1). Heat is conducted from the hot air to an inner surface of the photo-set resin model 31, elevating the temperature of the photo-set resin model 31 on an outer surface. This process is observed by the thermal image camera 34, recorded in a magnetic recording device (not shown) such as a hard disk of a personal computer or a video film (not shown), etc. and analyzed by the personal computer. The thermal strain generated in the photo-set resin model 31 by the hot air is detected by strain gauges 36 attached to a surface of the photo-set resin model 31, recorded in a magnetic recording device (not shown) of a static strain-measuring apparatus 38 and analyzed by the personal computer.

The present invention is described in further detail by the following Examples without intention of restricting the scope of the present invention.

Example 1, Comparative Example 1

As a thermal analysis model, a photo-set resin model (inner diameter: 46 mm, wall thickness: 2.5 mm) having a similar shape to that of a two-cylindered exhaust manifold shown in FIG. 1 was formed from a urethane acrylate resin by the method shown in FIG. 2. The resultant photo-set resin model had a thermal conductivity of 0.13 W/m·K. For comparison, a model of the same shape and size as those of the photo-set resin model was formed from a polyurethane foam.

Figure 4:
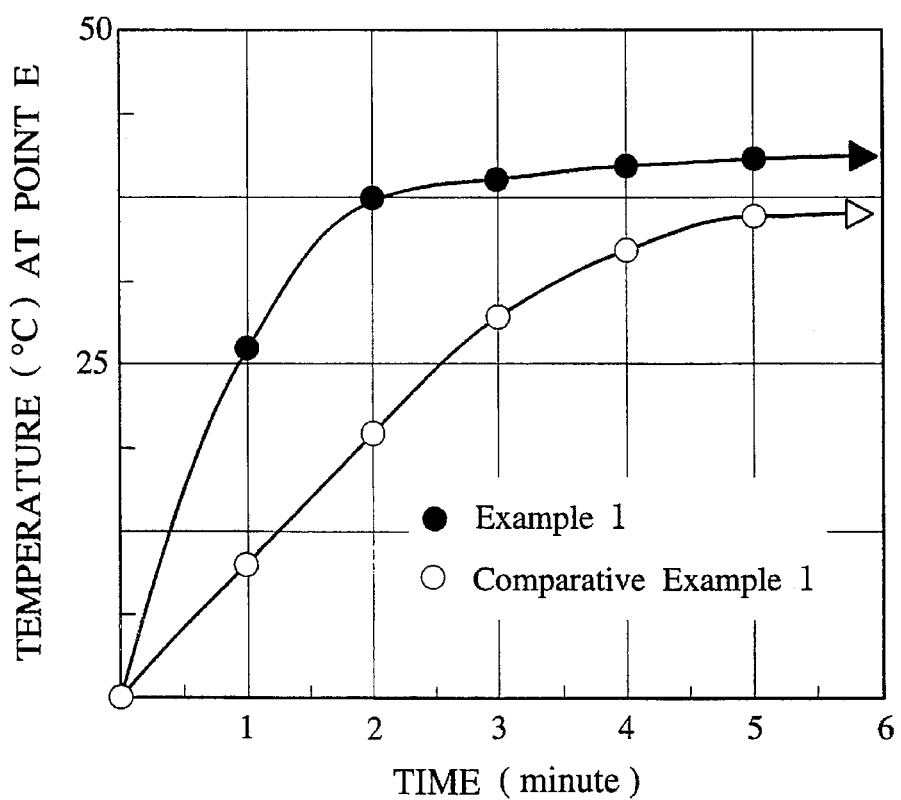
FIG. 4 is a graph showing the relation between a temperature at a point E and elapsed time when a hot air was introduced into the thermal analysis model of FIG. 1.

By introducing a hot air into each thermal analysis model, temperature elevation was measured at a point E (shown in FIG. 1) after each elapsed time. The results are shown in FIG. 4. As is shown in FIG. 4, the polyurethane foam model (Comparative Example 1) was heated slowly, taking about 5 minutes until the temperature at a point E leveled off to about 38° C. On the other hand, the photo-set resin model 1 of the present invention (Example 1) was heated rapidly, taking only about 3 minutes until the temperature at a point A leveled off to about 40° C. Accordingly, hot spots occurring at a point A were observed more clearly by using the photo-set resin model than by using the polyurethane foam model. The observation of the hot spots makes it possible to accurately predict the heat cracking of an actual heat-resistant member due to a thermal fatigue.

Figure 5:
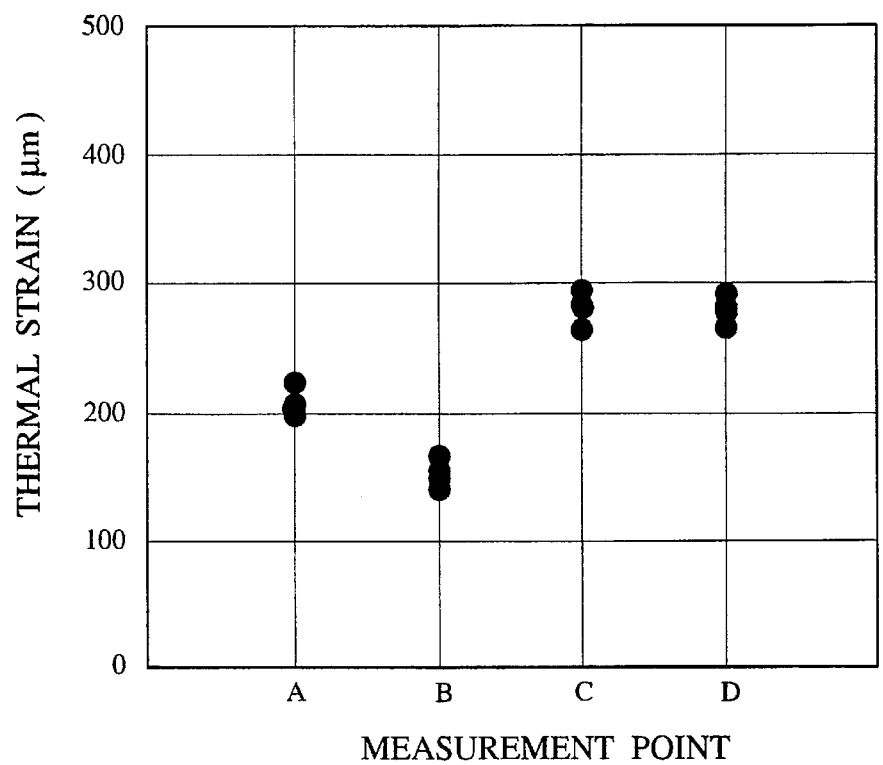
FIG. 5 is a graph showing thermal strain at points A, B, C and D when a hot air was introduced into the thermal analysis model of FIG. 1 on various days (under different test conditions)
Figure 6:
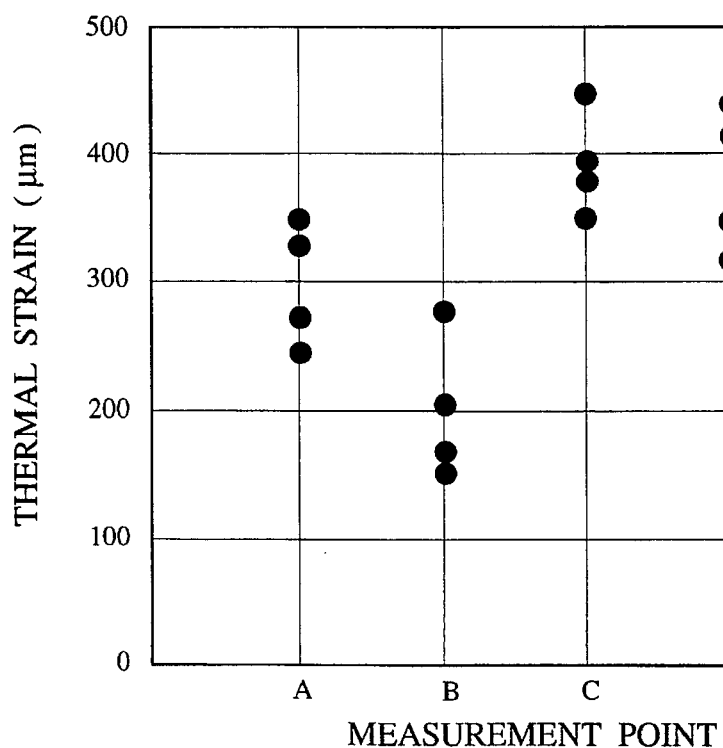
FIG. 6 is a graph showing thermal strain at points A, B, C and D when a hot air was introduced into a polyurethane foam model having the same shape as that of FIG. 1 on various days (under different test conditions)

To examine the influence of the temperature of a hot air on the thermal strain of the photo-set resin model, the thermal strain of the photo-set resin model was measured four times in totality at each point A, B, C and D with varied measurement dates (test atmosphere) while keeping the temperature of a hot air introduced into the photo-set resin model of FIG. 1 at 70° C. The measurement results are shown in FIG. 5 in the case of the photo-set resin model (Example 1) and in FIG. 6 in the case of the polyurethane foam model (Comparative Example 1). As is shown in FIGS. 5 and 6, the photo-set resin model shows better reproducibility than the polyurethane foam model in the measured values of thermal strain relative to the test atmosphere and the hot air temperature.

Example 2, Comparative Example 2

Figure 7:
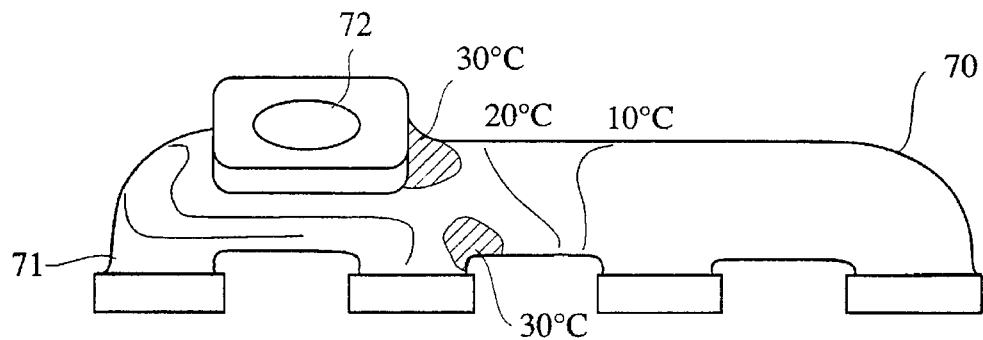
FIG. 7(a) is a schematic view showing a temperature distribution measured by a thermal image analyzer when a hot air at 70° C. was introduced into a photo-set resin model (after 60 seconds)
FIG. 7(b) is a schematic view showing a temperature distribution measured by a thermal image analyzer when a hot air at 70° C. was introduced into a photo-set resin model (after 180 seconds)
FIG. 7(c) is a schematic view showing a temperature distribution measured by a thermal image analyzer when a hot air at 70° C. was introduced into a photo-set resin model (after 300 seconds)
Figure 7:
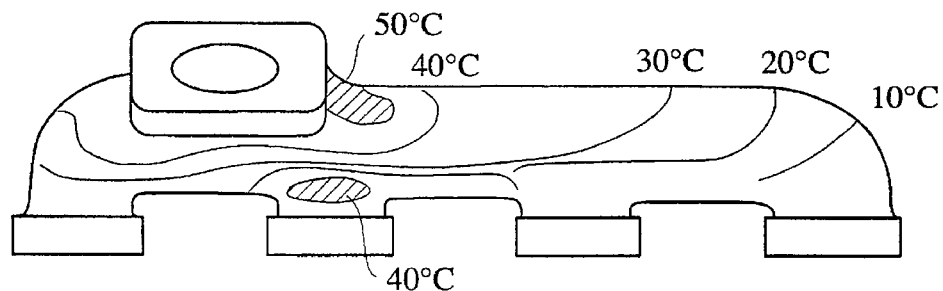
Figure 7:
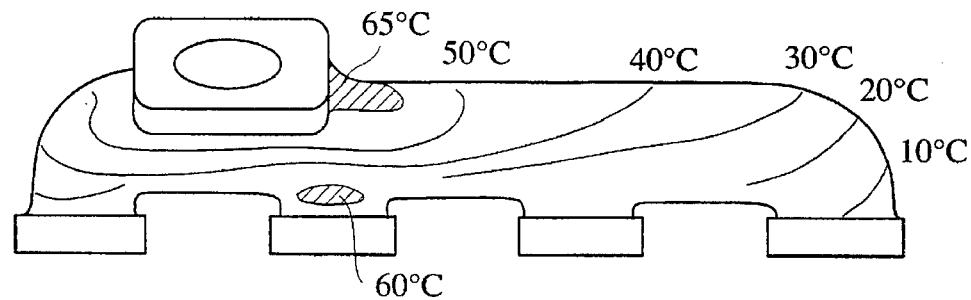

Using a photo-set resin model 70 (wall thickness: 3 mm) formed from a urethane acrylate resin and having a similar shape to that of a four-cylindered exhaust manifold, a hot air at 70° C. was introduced into four branch pipes 71 and discharged from a stem pipe 72 of the model 70 to the outside. The temperature distribution of the photo-set resin model 70 was measured by a thermal image analyzer 35 after each elapsed time of 60 seconds, 180 seconds and 300 seconds. The results are shown in FIGS. 7(a)–7(c).

Figure 8:
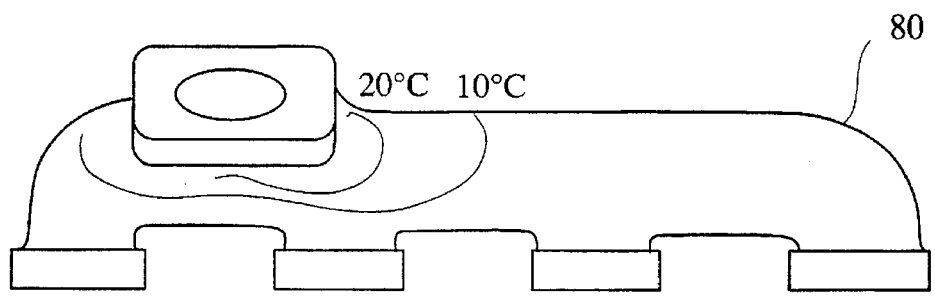
FIG. 8(a) is a schematic view showing a temperature distribution measured by a thermal image analyzer when a hot air at 70° C. was introduced into a polyurethane foam model having the same shape as that of the photo-set resin model of FIG. 7 (after 60 seconds)
FIG. 8(b) is a schematic view showing a temperature distribution measured by a thermal image analyzer when a hot air at 70° C. was introduced into a polyurethane foam model having the same shape as that of the photo-set resin model of FIG. 7 (after 180 seconds)
FIG. 8(c) is a schematic view showing a temperature distribution measured by a thermal image analyzer when a hot air at 70° C. was introduced into a polyurethane foam model having the same shape as that of the photo-set resin model of FIG. 7 (after 300 seconds).
Figure 8:
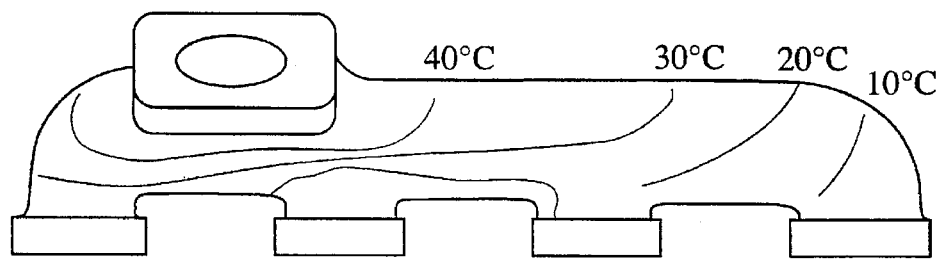
Figure 8:
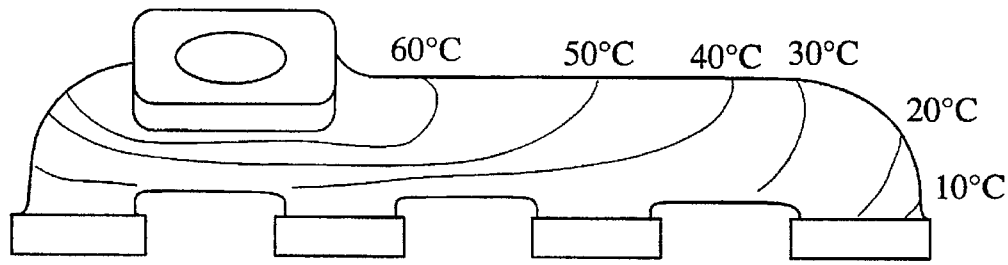

As in the case of the photo-set resin model 70, the measurement of a temperature distribution was conducted on a polyurethane foam model 80 after each elapsed time of 60 seconds, 180 seconds and 300 seconds. The results are shown in FIGS. 8(a)–8(c). Temperature elevation was observed in a wide area in the polyurethane foam model 80 (Comparative Example 2). On the other hand, the photo-set resin model 70 of the present invention (Example 2) showed substantially the same temperature distribution as that of the actual four-cylindered exhaust manifold, enabling clear observation of local hot spots (shown by the hatched portions) occurring during the temperature elevation due to air blowing. It is thus clear that the use of the photo-set resin model makes it possible to accurately predict the heat cracking portions of the exhaust manifold.

As described above in detail, since the thermal analysis model made of a photo-set resin has a larger thermal conductivity than a polyurethane foam model, the photo-set resin model is heated more rapidly, making the positions of hot spots clearer, and the measurement errors are small even though a measurement temperature atmosphere changes to some extent. Accordingly, the heat cracking positions of the heat-resistant member can be accurately located.

The method for predicting the heat cracking of a heat-resistant member using a photo-set resin model can provide the more accurate prediction of the transitionally occurring temperature distribution and thermal strain distribution than a polyurethane foam model method. Thus, the method of the present invention can accurately predict the positions of heat cracking which would occur in the heat-resistant member such as an actual exhaust manifold, etc. Accordingly, in the case of the heat-resistant member which may be subjected to heat cracking, the method of the present invention is helpful to achieve the desired design modification.

What is claimed is:

1. A model for predicting the heat-cracking of a heat resistant member, comprising:

a photo set resin formed in a shape similar to that of the heat-resistant member, having an inner wall and an outer surface, said resin having a thermal conductivity of 0.1–0.2 W/m·K, such that upon application of heat to said inner wall during a heat-cracking prediction operation, substantially no heat diffusion takes place during heat conduction from said inner wall to said outer surface and a transitional temperature change occurring in a period of time can be measured.

2. The model according to claim 1, wherein said photo-set resin is formed from a urethane acrylate resin.

3. A model for predicting the heat-cracking of a heat resistant member, comprising:

a photo set resin formed in a shape similar to that of the heat-resistant member, having an inner wall and an outer surface, said resin having a thermal conductivity of 0.1–0.2 W/M·K, such that upon application of heat to the inner wall during a heat-cracking prediction operation, substantially no heat diffuses to the outer surface.

* * * * *